United States Patent [19]
Yuan et al.

[11] Patent Number: 5,681,310
[45] Date of Patent: Oct. 28, 1997

[54] VERTEBRAL AUXILIARY FIXATION DEVICE HAVING HOLDING CAPABILITY

[76] Inventors: Hansen A. Yuan, 5066 Pine Valley Dr., Fayetteville, N.Y. 13066; Chih-I Lin, 14292 Spring Vista La., Chino Hills, Calif. 91709

[21] Appl. No.: 549,908

[22] Filed: Oct. 30, 1995

Related U.S. Application Data

[63] Continuation of Ser. No. 277,766, Jul. 20, 1994, abandoned.

[51] Int. Cl.$^6$ ............................. A61B 17/56; A61B 17/08
[52] U.S. Cl. ............................. 606/61; 606/151; 606/72
[58] Field of Search ............................. 606/151, 154, 606/77, 74, 61, 60, 69, 70, 71

[56] References Cited

U.S. PATENT DOCUMENTS

| | | | |
|---|---|---|---|
| 3,463,158 | 8/1969 | Schmitt et al. | 606/151 |
| 3,710,789 | 1/1973 | Ersek | 606/60 |
| 4,570,623 | 2/1986 | Ellison et al. | 606/75 |
| 4,820,305 | 4/1989 | Harms et al. | 606/61 |
| 5,084,051 | 1/1992 | Törmälä et al. | 606/77 |
| 5,102,421 | 4/1992 | Anspach et al. | 606/60 |
| 5,108,395 | 4/1992 | Laurain | 606/61 |
| 5,156,616 | 10/1992 | Meadows et al. | 606/73 |
| 5,344,421 | 9/1994 | Crook | 606/61 |
| 5,346,492 | 9/1994 | Morgan | 606/60 |
| 5,443,483 | 8/1995 | Kirsch | 606/151 |
| 5,527,311 | 6/1996 | Procter et al. | 606/61 |

FOREIGN PATENT DOCUMENTS

| | | | |
|---|---|---|---|
| 0507162 | 10/1992 | European Pat. Off. | 606/60 |
| 2612392 | 9/1988 | France | 606/77 |

*Primary Examiner*—Michael Buiz
*Assistant Examiner*—Julian W. Woo

[57] ABSTRACT

A vertebral auxiliary fixation device comprises a holding mat and a plurality of fastening elements. The holding mat is fastened by the fastening elements to a vertebra such that the holding mat covers the outer side of a foreign object which is implanted in the vertebra, and that the holding mat prevents the implanted foreign object from jutting out of the vertebra. The holding mat and the fastening elements are made of a material capable of being assimilated into the tissues of a human body.

10 Claims, 2 Drawing Sheets

5,681,310

VERTEBRAL AUXILIARY FIXATION DEVICE HAVING HOLDING CAPABILITY

This application is a continuation of application Ser. No. 08/277,766, filed Jul. 20, 1994, now abandoned.

FIELD OF THE INVENTION

The present invention relates generally to a vertebral fixation device, and more particularly to a vertebral auxiliary fixation device capable of holding an implanted graft or filling.

BACKGROUND OF THE INVENTION

In the surgical process of fixing and retrieving a deformed vertebra, it is often required of a surgeon to implant a foreign object, such as a bone graft or a filling of hydroxylapitite, in a vertebra intended to be fixed or between the vertebrae intended to be fixed. It is imperative that the bone graft or filling must be implanted such that it is not permitted to jut out of the vertebra in which it is implanted or the vertebrae between which it is implanted. It is conceivable that the tissues contiguous to the vertebra in which the bone graft or filling is implanted, or the tissues contiguous to the vertebrae between which the bone graft or filling is implanted, are often vulnerable to injury caused by the jutted bone graft or filling. In addition, the patient receiving the treatment is often troubled by a severe pain which is brought about by the jutted graft or filling that happens to touch the nerve. The conventional method of preventing the implanted bone graft or filling from jutting out involves the use of a bone plate, which is placed on the implanted bone graft or filling. However, such a conventional method as described above is defective in design in that the bone plate hampers the surgical operation, and that the bone plate can not be fastened intimately with the vertebra intended to be fixed, and further that the fastening screws can be caused to loosen to result in the detachment of the implanted bone graft or filling.

SUMMARY OF THE INVENTION

It is therefore the primary objective of the present invention to provide a vertebral auxiliary fixation device, which has the effect of holding a foreign object implanted into a vertebra intended to be fixed or between the vertebrae intended to be fixed.

It is another objective of the present invention to provide a vertebral auxiliary fixation device, which has a holding capability and is composed of a holding mat and fastening elements.

In keeping with the principle of the present invention, the foregoing objectives of the present invention are attained by the vertebral auxiliary fixation device which comprises a holding mat and a plurality of fastening elements. The holding mat is used to cover the outer side of a foreign object which is implanted in a vertebra intended to be fixed and which is thus prevented from being detached from the vertebra. The holding mat is fastened securely to the vertebra by the fastening elements.

The holding mat of the present invention is made of a flexible and biocompatible material, such as material sold under the trademark DACRON, and surgical sutures. The flexible and biocompatible material of little expandability is recommended. The holding mat may be either woven or nonwoven. In addition, the holding mat may be of any shape or size as long as it is capable of holding a foreign object implanted in a vertebra intended to be fixed or between vertebrae intended to be fixed. In general, the holding mat of the present invention is preferably rectangular in shape, with each of the four corners thereof being arcuate.

The fastening elements are intended to fasten the holding mat securely to a vertebra to be fixed. The commonly used fastening elements include the small bone screws, the stringed bone screws, the bone screws with a single inverted hook, the bone screws with multiple inverted hooks, the stringed and inverted hooks, etc. In order to enhance the effect of fastening the holding mat by the fastening elements to the vertebra intended to be fixed, it is suggested that a pad or even a pad having thorns be disposed between the fastening elements and the holding mat. The fastening elements of the present invention are made of implantable metal materials, such as iron-based stainless steel 316LVM, Ti-6-4, cobalt-nickel alloy, etc. The string of the fastening elements of the present invention may be either single-stranded or multistranded; it is generally made of a medically accepted threaded material such as that sold under the trademark Dacron.

It must be noted here that the holding mat and the fastening elements of the present invention may be made of a biocompatible material similar to that which is used in making the artificial ligaments, and that the holding mat and the fastening elements of the present invention can be therefore assimilated by the human body.

A few months after the surgical operation in which a bone graft or filling is implanted in a vertebra under treatment or between two vertebrae under treatment, the implanted bone graft or filling has already been joined with the vertebra or the vertebrae. As a result, there is no need to provide any additional auxiliary fixation device for preventing the implanted bone graft or filling from jutting out of the vertebra or the vertebrae. In the meantime, the holding mat and the fastening elements of the vertebral auxiliary fixation device of the present invention will be absorbed and incorporated gradually and completely into the body of a patient receiving the treatment, thereby reducing the risk that the implanted foreign object becomes a factor hazardous to the health of the patient.

DETAILED DESCRIPTION OF THE INVENTION

Figure 1:
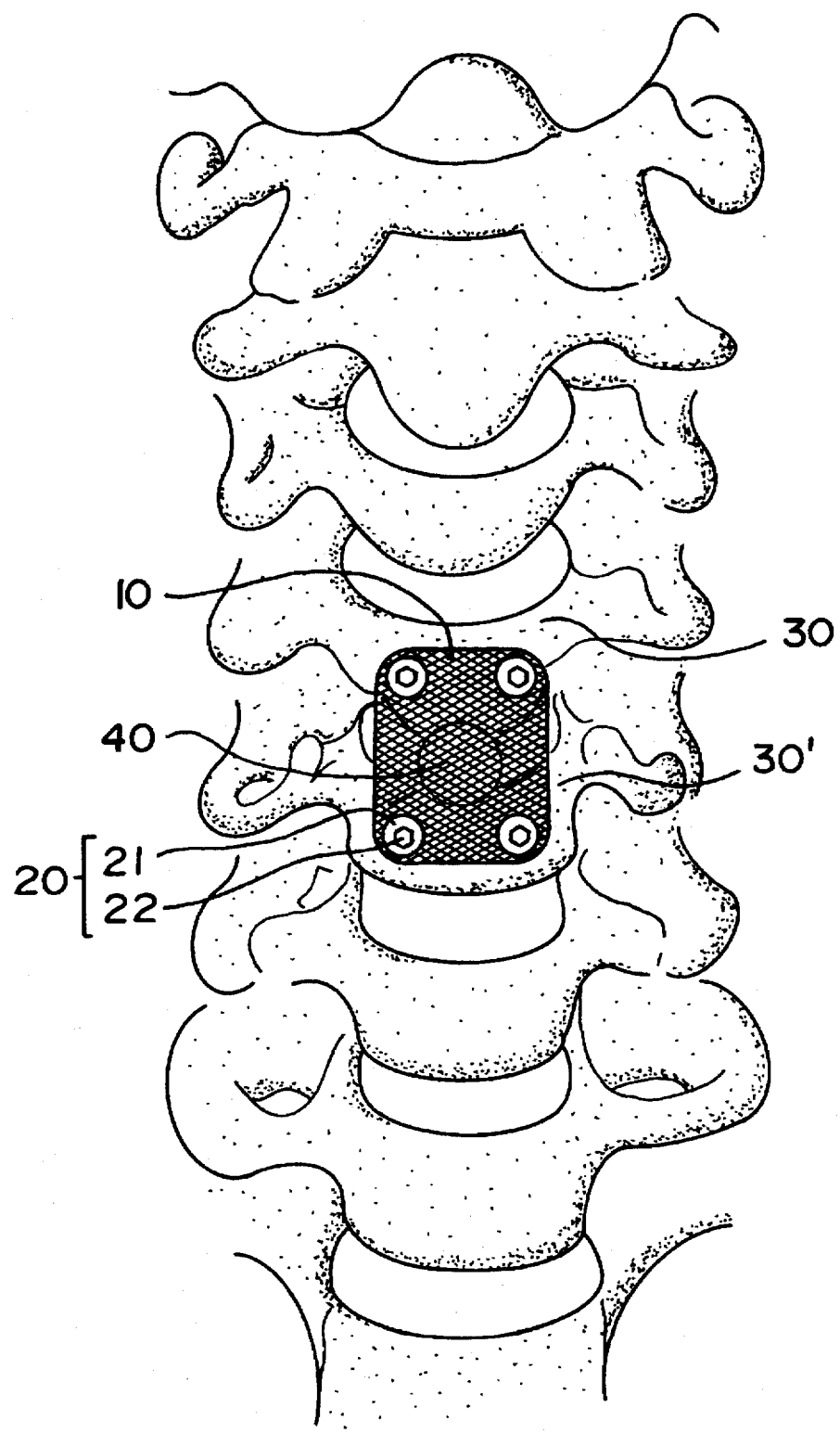
FIG. 1 is a schematic view showing that a vertebral auxiliary fixation device embodied in the present invention is fastened onto two vertebrae in which an interbody fusion system is implanted.

As shown in FIG. 1, a holding mat 10 and a plurality of fastening screws 20 of the vertebral auxiliary fixation device of the present invention are fastened onto two vertebrae 30 and 30' which are intended to be fixed by an interbody fusion system 40 corresponding in definition to the foreign object mentioned previously in this specification. Each of the fastening screws 20 has a head 21 provided therein with a tool hole 22 of a hexagonal construction. The holding mat 10 is fastened securely with the vertebrae 30 and 30' by a plurality of fastening screws 20, which are fastened onto the vertebrae 30 and 30' by means of a hexagonal wrench engageable with the hexagonal tool holes 22 of the heads 21 of the fastening screws 20. The interbody fusion system 40 is implanted in the vertebrae 30 and 30' such that the interbody fusion system 40 is held securely under the holding mat 10, and that the implanted interbody fusion system 40 is therefore prevented from jutting out of the vertebrae 30 and 30'.

Figure 2:
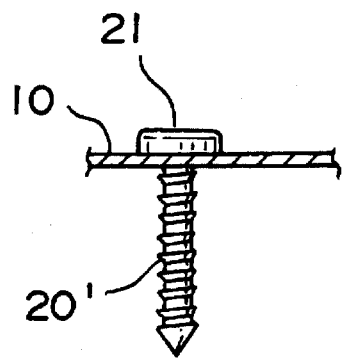
FIG. 2 is a sectional view showing a first type of fastening element which can be used to secure the mat of the vertebral auxiliary fixation device according to the present invention.
Figure 3:
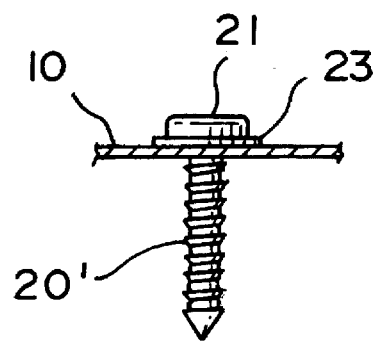
FIG. 3 is a cross-sectional view of the fastening element depicted in FIG. 2 with the inclusion of a pad.
Figure 4:
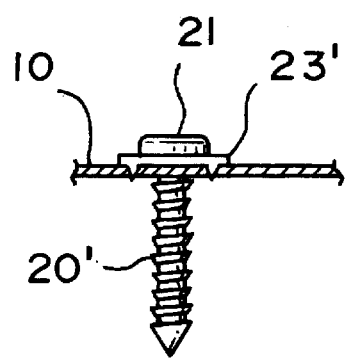
FIG. 4 is a sectional view showing the fastening element of FIG. 2, along with a thorny pad.
Figure 5:
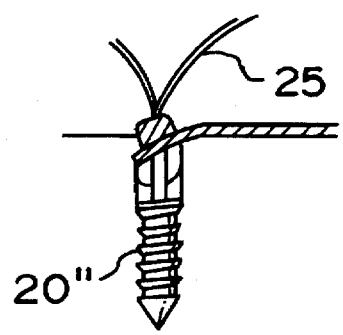
FIG. 5 is a sectional view showing another type of fastening element for use with the present invention.
Figure 6:
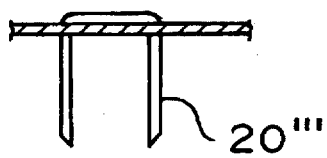
FIG. 6 is a sectional view illustrating a still further fastening element for use in accordance with the present invention.

The fastening elements of the vertebral auxiliary fixation device of the present invention may be of various forms, as shown in FIGS. 2–6. For example, bone screws are used as fastening element main bodies 20', as shown in FIGS. 2–4. The fastening element main body 20" may be also provided with a fastening cord 25, as shown in FIG. 5. A staple-shaped fastening element main body 20' is shown in FIG. 6. It must be noted here that a pad 23 or a thorny pad 23' may be placed between the holding mat 10 and the head 21 of the fastening element 20 for enhancing the effect of fastening the holding mat 10 by the fastening element 20, as shown in FIGS. 3 and 4. The fastening cord 25 of the fastening element main body 20", as shown in FIG. 5 is intended for enhancing the effect of fastening the holding mats 10 by the fastening elements 20.

The embodiments of the present invention described above are to be regarded in all respects as merely illustrative and not restrictive. Accordingly, the present invention may be embodied in other specific forms without deviating from the spirit thereof. The present invention is therefore to be limited only by the scope of the following appended claims.

What is claim is:

1. A method of mending a deformed vertebra comprising: preparing a vertebra for implantation of a foreign object; implanting a foreign object into the vertebra; covering an outer side of the foreign object with a mat made from a flexible, biocompatible material; and fastening the mat in place by inserting a plurality of fastening elements through the flexible biocompatible material and into the vertebra to prevent the foreign object from jutting out of the vertebra.

2. The method according to claim 1, further comprising: providing the mat in rectangular form with arcuate corners.

3. The method according to claim 1, further comprising: forming the mat of a material which is absorbable into tissues of a human body.

4. The method according to claim 1, further comprising: forming the mat of a woven material.

5. The method according to claim 1, further comprising: forming the mat of a non-woven material.

6. The method according to claim 1 wherein the step of fastening the mat in place comprises inserting a plurality of headed fastening screws through the biocompatible material and into the vertebra.

7. The method according to claim 6 comprising the additional step of inserting a pad between the heads of the headed fastening screws and the biocompatible material.

8. The method according to claim 6 comprising the additional step of inserting a thorny pad between the head of the headed fastening screws and the biocompatible material.

9. The method according to claim 1 wherein the step of fastening the mat in place comprises inserting a plurality of threaded fastening screws having fastening cords through the biocompatible material and into the vertebra.

10. The method according to claim 1 wherein the step of fastening the mat in place comprises inserting substantially "U"-shaped fastening elements through the biocompatible material and into the vertebra.

* * * * *